(12) United States Patent
Kitamura et al.

(10) Patent No.: US 6,890,735 B2
(45) Date of Patent: May 10, 2005

(54) TSG-LIKE GENE

(75) Inventors: Toshio Kitamura, Tokyo (JP); Sumiyo Morita, Tokyo (JP)

(73) Assignees: Chugai Seiyaku Kabushiki Kaisha, Tokyo (JP); Kitamura, Toshio, Tokyo (JP)

( * ) Notice: Subject to any disclaimer, the term of this patent is extended or adjusted under 35 U.S.C. 154(b) by 11 days.

(21) Appl. No.: 10/092,925

(22) Filed: Mar. 6, 2002

(65) Prior Publication Data

US 2002/0168721 A1 Nov. 14, 2002

Related U.S. Application Data

(63) Continuation-in-part of application No. PCT/JP00/06050, filed on Sep. 6, 2000.

(30) Foreign Application Priority Data

Sep. 6, 1999 (JP) ............................................ 11/252190

(51) Int. Cl.[7] .......................... C12P 21/06; C12N 15/74; C12N 5/92; C07H 21/04; C07K 14/00
(52) U.S. Cl. ................... 435/69.1; 435/320.1; 435/325; 536/23.5; 530/350
(58) Field of Search ............................ 435/69.1, 320.1, 435/325; 530/350; 536/23.5

(56) References Cited

U.S. PATENT DOCUMENTS

| | | | |
|---|---|---|---|
| 6,008,022 A | * 12/1999 | Su et al. ..................... | 435/69.4 |
| 2002/0038468 A1 | 3/2002 | Leviten | |
| 2002/0046413 A1 | 4/2002 | Allen | |
| 2002/0108138 A1 | 8/2002 | Guenther | |
| 2002/0127712 A1 | 9/2002 | Brennan | |

FOREIGN PATENT DOCUMENTS

| | | |
|---|---|---|
| AU | 5369296 A | 10/1997 |
| AU | 7165601 A | 1/2002 |
| CA | 2249251 A1 | 9/1997 |
| CA | 2416292 A1 | 1/2002 |
| EP | 0907719 A1 | 4/1999 |
| EP | 1304921 A2 | 5/2003 |
| WO | WO 97/34998 A1 | 9/1997 |
| WO | WO 98/46641 | 10/1998 |
| WO | WO 99/38976 | 8/1999 |
| WO | WO 02/01950 A3 | 1/2002 |
| WO | WO 02/01950 A2 | 1/2002 |

OTHER PUBLICATIONS

Mason et al., "Dorsal midline fate in *Drosophila* embryos requires *twisted gastrulation*, a gene encoding a secreted protein related to human connective tissue growth factor", *Genes and Development*, vol. 8, pp. 1489–1501, 1994.
Marra, M., et al., EMBL Accession No. AA959672 (created May 11, 1998, updated Mar. 3, 2000).
Zakin, et al., EMBL Accession No. AF292033 (created Aug. 17, 2000).
Marra, M., et al., EMBL Accession No. AI391008 (created Feb. 4, 1999, updated Mar. 16, 2000).
Graf, et al., EMBL Accession No. AJ297390 (created Aug. 29, 2000, updated Aug. 2, 2001).
Nosaka, T. et al., "Mammalian Twisted Gastrulation Is Essential for Skeleto–Lymphogenesis" *Molecular and Cellular Biology*, 23(8):2969–2980 (Apr. 2003).
Oelgeschläger, M. et al., "The evolutionarily conserved BMP–binding protein Twisted gastrulation promotes BMP signalling" *Nature*, 405(6788):757–763 (Jun. 15, 2000).
Nosaka et al., Mammalian twisted gastrulation is essential for skeleto–lymphogenesis, Moecular and Cellular Biology, 23:2969–2980 (2003).
Graf et al., Evolutionary conservation, developmental expression, and genomic mapping of mammalian *Twisted gastrulation*, Mammalian Genome, 12:554–560 (2001).
Chang et al., Twisted gastrulation can function as a BMP antagonist, Nature, 410:483–487 (2001).
Ross et al., Twisted gastrulation is a conserved extracellular BMP antagonist, Nature 410:479–483 (2001).
Scott et al., Homologues of Twisted gastrulation are extracellular cofactors in antagonism of BMP Signalling, Nature 410:475–478 (2001).

* cited by examiner

*Primary Examiner*—Janet Andres
(74) *Attorney, Agent, or Firm*—Fish & Richardson, PC

(57) ABSTRACT

A gene encoding a novel protein that is homologous to *Drosophila* TSG was isolated from a cDNA library derived from the AGM region of mouse embryos by using an originally developed cloning method specific to a gene encoding a membrane secretory protein. This gene is useful in developing drugs that regulate hematopoietic stem cell generation, immune and hematopoietic functions, etc.

30 Claims, 1 Drawing Sheet

1st Amino Acid Sequence
    File Name        : clone 106.full.seq.protein
    Sequence Size    : 222
2nd Amino Acid Sequence
    File Name        : TSG.protein
    Sequence Size    : 249
[33.3% / 216 aa]

```
   1' MKSHYIVLALASLTFLLCLPVSQSCNKALCASDVSKCLIQELCQCRPGEGNCPCCKECM
      *.*.  .....    .*. ...**...*.* ******  .***. ..  *.***.*.
   1" MQLLCYFVILFVGIAPWSSLANDDGCNEVVCGSVVSKCLITQSCQCKLND—CHCCKDCL

60' LCLGALWDECCDCVGMCNPRNYSDTPPTSKSTVEELHEPIPSLFRALTEGDTQLNWNIVS
      ***.*. ***.*..**   ..  *..*.....  *.*.** .**..*.. .*....
  59" NCLGELYIECCGCLDMCPKHKDVLPSLTPRSEIGDI-EGVPELFDTLTAEDDE-GWSTIR

120' FPVAEELSHHENLVSFLETVNQLHHQNVSVPSNNVHAPFPSDKERMCTVVYFDDCMSIHQ
      *..  ...... .        .. .. ..*  ..   *.    .***.* ..*..  ..
 117" FSMRAGFKQR—V————————QGGASGDAGNGNGNGNAGSAGVTLCTVIYVNSCIRANK

180' CKISCESMGASKYRWFHNACCECIGPECIDYGSKTVKCMNCMF
      *. *******.*****..****.* .*..** .. .*..*
 166" CRQQCESMGASSYRWFHDGCCECVGENCLNYGINESRCRGCPEDQDQLLTADTVPAEAEQ
```

FIG. 1

TSG-LIKE GENE

This application is a continuation-in-part of International Patent Application No. PCT/JP00/06050, filed Sep. 6, 2000, which claims priority to Japanese Patent Application No. 11-252190, filed Sep. 6, 1999.

TECHNICAL FIELD

The present invention relates to a novel TSG-like protein and its gene derived from the AGM region of mouse embryos.

BACKGROUND

In the early fetal period of mice, hematopoiesis is carried out in the yolk sac and fetal liver. Hematopoiesis in the yolk sac is referred to as fetal hematopoiesis during which primarily nucleated fetal erythrocytes are produced. On the other hand, hematopoiesis in the fetal liver is referred to as adult hematopoiesis during which all lines of blood cells are produced with the exception of nucleated fetal erythrocytes.

Although the activity that causes the production of all lines of blood cells, that is the long-term repopulating hematopoietic stem cell (LTR-HSC) activity of hematopoietic stem cells, is not detected in fetal hematopoiesis, it is detected in adult hematopoiesis. It is now thought that the cells having this LTR-HSC activity are actually produced not initially in the liver, but in the aorta-gonad-mesonephros (AGM) region at day 10–11 of embryogenesis. During this period, these cells are thought to also proliferate in this AGM region, after which they migrate to the fetal liver (Medvinsky et al., Cell 86:897–906). Thus, a gene that is important for the generation of hematopoietic stem cells may be expressed in this AGM region.

SUMMARY

The present invention provides a novel TSG-like protein and its gene derived from the AGM region of mouse embryos. In addition, the present invention also provides a vector into which the gene is inserted, a host cell carrying the vector, and an antibody that binds to the protein. Moreover, the present invention provides a method for screening compounds, such as receptors, that bind to the protein by using the protein.

The present inventors screened cDNA that encode secretory/membrane proteins to search for a gene having a novel signal sequence from the AGM region of mouse embryos, using poly(A) RNA derived from this AGM region as the starting material, and an originally-developed signal sequence trap (SST) method (Japanese Patent Application No. Hei 9-324912). As a result, the present inventors succeeded in isolating a gene that encodes a novel protein homologous to *Drosophila* TSG gene. TSG gene is one of the dorsal determining factors of an embryo, and is known to determine differentiation of dorsal midline cells due to interaction with DPP (the counterpart of BMP2/4) (Mason et al., Genes and Development 8:1489–1501). Since TSG protein has been reported to bind to BMP (Oelgeschlager et al., Nature 405:757–763, 2000), the isolated TSG-like gene, which is structurally similar to the TSG gene, is predicted to interact with BMP2/4. In addition, the fact that this TSG-like gene was isolated from the AGM region of mouse embryos suggests its involvement in the generation of hematopoietic stem cells. Thus, the TSG-like protein of the present invention is useful as a tool for purifying and screening factors involved in the generation of hematopoietic stem cells, and the screening of drug candidate compounds for immune and hematopoietic system-related diseases.

The present invention relates to a novel TSG-like protein, its gene, as well as the production and uses of the protein and gene. More specifically, the present invention relates to:

(1) a DNA according to any one of (a) to (d):

(a) a DNA encoding a protein comprising the amino acid sequence of SEQ ID NO:2, (b) a DNA comprising the coding region of the nucleotide sequence of SEQ ID NO:1, (c) a DNA comprising an amino acid sequence in which one or more amino acids of the amino acid sequence of SEQ ID NO:2 has been substituted, deleted, inserted and/or added, wherein said DNA encodes a protein that is functionally equivalent to the protein comprising the amino acid sequence of SEQ ID NO:2, and, (d) a DNA hybridizing to a DNA that comprises the nucleotide sequence of SEQ ID NO:1 under stringent conditions, and, encodes a protein functionally equivalent to the protein comprising the amino acid sequence of SEQ ID NO:2;

(2) a DNA encoding a partial peptide of the protein comprising the amino acid sequence of SEQ ID NO:2;

(3) a vector into which the DNA according to (1) or (2) has been inserted;

(4) a transformant carrying the DNA according to (1) or (2) or the vector according to (3);

(5) a protein or peptide encoded by the DNA according to (1) or (2);

(6) a method for producing the protein or peptide according to (5), comprising the steps of culturing the transformed cell according to (4), and recovering the expressed protein from said cell or the culture supernatant;

(7) an antibody against the protein according to (5);

(8) a oligonucleotide that hybridizes to the DNA comprising of the nucleotide sequence of SEQ ID NO:1, or the complementary strand thereof, and, comprises at least 15 nucleotides;

(9) a method of screening for a compound having the activity of binding to the protein according to (5), comprising the steps of:

(a) contacting a test sample with the protein or partial peptide according to (5), and, (b) selecting a compound having an activity of binding to the protein or partial peptide according to (5); and,

(10) a compound isolated using a method as set forth in (9), having an activity of binding to the protein according to (5).

The present invention relates to a novel protein that is homologous to the *Drosophila* TSG gene. A mouse-derived cDNA nucleotide sequence isolated by the present inventors is shown in SEQ ID NO:1, while the amino acid sequence of the protein encoded by the cDNA is shown in SEQ ID NO:2. This protein has a signal sequence at its N terminus, and is homologous to TSG protein, a dorsal determining factor of the *Drosophila* embryo. As a result of Northern blot analysis of mRNA derived from mouse tissues, a signal of about 4.0 kb was observed in the heart, lung, liver, and kidney. In addition, this signal was also confirmed to be expressed in 9, 10, 11, 12, and 13-day viviparity. The isolation from the AGM region of the embryo, expression in early embryos, homology to TSG protein and presumed interaction with BMP2/4, the fact that BMP2/4 is required for the differentiation of blood cell lines, the fact that TSG protein binds to BMP to promote signaling activity of BMP (Oelgeschlager et al., Nature 405:757–763, 2000), all suggest that this protein may be involved in the differentiation of hematopoietic cells as well as bone formation, and so forth. Thus, this protein can be utilized as a tool for purifying and cloning proteins related to hematopoietic stem cell formation, bone formation, and so forth, and for screening drug candidate compounds as therapeutic agents for immune and hematopoietic system-related diseases, bone formation-related diseases, and such.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NO:2. The invention also includes a polypeptide, or fragment thereof, that differs from the corresponding sequence shown as SEQ ID NO:2. The differences are, preferably, differences or changes at a non-essential residue or a conservative substitution. In one embodiment, the polypeptide includes an amino acid sequence at least about 60% identical to a sequence shown as SEQ ID NO:2, or a fragment thereof. Preferably, the polypeptide is at least 65%, 70%, 75%, 80%, 85%, 90%, 95%, 98%, 99% or more identical to SEQ ID NO:2 and has at least one TSG-like function or activity described herein. Preferred polypeptide fragments of the invention are at least 10%, preferably at least 20%, 30%, 40%, 50%, 60%, 70%, or more, of the length of the sequence shown as SEQ ID NO:2 and have at least one TSG-like function or activity described herein. Or alternatively, the fragment can be merely an immunogenic fragment.

In addition, the present invention also includes proteins that are functionally equivalent to the protein described in SEQ ID NO:2. Such proteins include, for example, homologous proteins of other organisms corresponding to the protein described in SEQ ID NO:2, as well as mutants of the protein. In the present invention, the term "functionally equivalent" means that the target protein has an activity for rescuing aberrations in the differentiation of dorsal midline cells when injected into a TSG mutant of *Drosophila*, or an activity that regulates embryo development (for example, dorsoventral induction capability) when injected into Xenopus eggs. In addition, the protein of the present invention is also suggested to have the function of promoting the signaling activity of BMP (bone morphogenetic protein; DPP) by binding with BMP (Oelgeschlager et al., Nature 405:757–763, 2000).

One method for isolating such proteins well known to those skilled in the art is to introduce mutations into the proteins. For example, one skilled in the art can prepare proteins functionally equivalent to the protein of SEQ ID NO:2 by introducing appropriate mutations into the amino acid of SEQ ID NO:2, by using site-specific mutagenesis (Hashimoto-Gotoh et al., Gene 152:271–275, 1995; Zoller et al., Methods Enzymol. 100:468–500, 1983; Kramer et al., Nucleic Acids Res. 12:9441–9456, 1984; Kramer et al, Methods Enzymol. 154:350–367, 1987; Kunkel, Proc. Natl. Acad. Sci. USA 82:488–492, 1985; Kunkel Methods Enzymol. 85:2763–2766, 1988). Mutation of amino acids may occur in nature, too. The protein of the present invention also includes a protein comprising the amino acid sequence of SEQ ID NO:2 in which one or more amino acids are mutated, wherein the resulting "mutant" protein is functionally equivalent to the protein of SEQ ID NO:2. In such a mutant protein, the number of the amino acids mutated are considered to be usually 30 residues or less, preferably 15 residues or less, more preferably 5 residues or less, and still preferably, 3 residues or less.

The mutated amino acid residue is preferably mutated into an amino acid that allows the properties of the amino acid side-chain to be conserved. Examples of properties of amino acid side chains include: hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom-containing side-chain (C, M); a carboxylic acid- and amide-containing side-chain (D, N, E, Q); a nucleotide-containing side-chain (R, K, H); and an aromatic-containing side-chain (H, F, Y, W)(the letters within the parentheses indicate the one-letter codes of amino acids).

It is well known that a protein having a deletion, addition, and/or substitution of one or more amino acid residues in the sequence of the protein can retain the original biological activity (Mark et al., Proc. Natl. Acad. Sci. USA 81:5662–5666, 1984; Zoller et al., Nucleic Acids Res. 10:6487–6500, 1982; Wang et al., Science 224:1431–1433; Dalbadie-McFarland et al., Proc. Natl. Acad. Sci. USA 79:6409–6413, 1982).

A protein having the amino acid sequence of SEQ ID NO:2, to which one or more amino acid residues have been added, is exemplified by a fusion protein containing the protein of SEQ ID NO:2. Fusion proteins, in which the protein listed in SEQ ID NO:2, or its partial peptide is fused to other peptides or proteins, are included in the present invention. Fusion proteins can be made using well-known techniques by linking the DNA encoding the protein of the invention in frame with the DNA encoding another peptide or protein, followed by inserting the DNA into an expression vector, and expressing it in a host. There is no restriction as to the peptides or proteins to be fused to the protein of the present invention.

Other known peptides that can be used for fusion with the protein of the present invention include, for example, FLAG (Hopp et al., BioTechnology 6:1204–1210, 1988), 6× His comprised of six His (histidine) residues, 10× His, influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, etc. In addition, examples of other proteins used for fusion with the protein of the present invention include, for example, GST (glutathione-S-transferase), HA (influenza agglutinin), immunoglobulin constant region, β-galactosidase, MBP (maltose binding protein), etc.

Fusion proteins can be prepared by fusing DNA encoding these commercially available peptides or proteins with DNA encoding the protein of the present invention and expressing the prepared fused DNA.

An alternative method for isolating functionally equivalent proteins known to those skilled in the art is, for example, a method utilizing the hybridization technique (Sambrook et al., Molecular Cloning 2nd ed. 9.47–9.58, Cold Spring Harbor Lab. Press, 1989). Generally, one skilled in the art can isolate DNAs highly homologous to the whole or part of the DNA sequence encoding the protein of SEQ ID NO:2 or 4 (SEQ ID NO:1 or 3, respectively), and then isolate a DNA that codes for a protein functionally equivalent to the protein of SEQ ID NO:2 or 4 from the DNA isolated. The proteins of the present invention thus include proteins encoded by DNA that hybridize with the whole or part of the DNA sequence encoding the protein of SEQ ID NO:2 or 4, wherein the proteins are functionally equivalent to the protein of SEQ ID NO:2 or 4. These proteins include homologues from mammals except mice (for example, a protein encoded by a human gene).

Hybridization for isolating a DNA encoding a functionally equivalent protein can be carried out under the stringent conditions of, for example, 10% formamide, 5×SSPE, 1× Denhardt's solution, and 1×salmon sperm DNA. More preferable (more stringent) conditions are, 25% formamide, 5×SSPE, 1× Denhardt's solution, and 1×salmon sperm DNA, and even more preferable (even more stringent) conditions are, 50% formamide, 5×SSPE, 1× Denhardt's solution, and 1× salmon sperm DNA. However, several factors are thought to influence the stringency of hybridization other than the above-described formamide concentration, and one skilled in the art can suitably select these factors to accomplish a similar stringency. Also, instead of hybridization, it is also possible to isolate a DNA encoding a functionally equivalent protein by a gene amplification method such as PCR using a portion of the DNA encoding the protein (SEQ ID NO:1) as a primer.

The proteins encoded by DNA isolated by hybridization or gene amplifying techniques having functions equivalent to the protein of SEQ ID NO:2 are usually highly homologous to the protein of SEQ ID NO:2 at the amino acid sequence level. The protein of the present invention also includes a protein that is functionally equivalent to the protein of SEQ ID NO:2 and has a high homology to the amino acid sequence indicated in SEQ ID NO:2. "High homology" refers to an amino acid sequence identity of 40% or more, preferably 50% or more, and more preferably 60% or more. The algorithm described in the literature (Wilbur et al., Proc. Natl. Acad. Sci. USA 80:726–730, 1983) may be used for determining protein homology.

The protein of the present invention may be different in the amino acid sequence, molecular weight, isoelectric point, presence or absence of a sugar chain, or the form of the sugar chain, and so forth depending on the cells that produce it, the host, or purification process (described later). However, such proteins are included in the present invention provided the resulting protein is functionally equivalent to the protein described in SEQ ID NO:2. For example, when the protein of the present invention is expressed in prokaryotic cells, for example, E. coli, a methionine residue is added to the N-terminus of the amino acid sequence of the original protein. Alternatively, when expressed in eukaryotic cells, for example, mammalian cells, the N-terminus signal sequence is removed. The protein of the present invention also includes such proteins. As a result of analyzing the amino acid sequence of the protein of the present invention, the signal sequence was estimated to extend from Met at position 1 to Ser at position 24 in the amino acid sequence of SEQ ID NO:2. Thus, the present invention includes proteins comprising amino acids from Cys at position 25 to Phe at position 222 in the amino acid sequence described in SEQ ID NO:2.

The protein of the present invention can be prepared as a recombinant protein or as a naturally-occurring protein by methods known to those skilled in the art. If it is a recombinant protein, the protein is secreted extracellularly as, for example, a soluble protein. Subsequently, the culture supernatant of the cells can be recovered, concentrated and then purified by chromatography utilizing ion exchange, reverse phase, or gel filtration chromatography, or by affinity chromatography using a column in which an antibody against the protein of the present invention is immobilized, or by a combination of these columns. Alternatively, the protein of the invention can be prepared by expressing the protein in host cells (e.g., animal cells or E. coli) as a fusion protein with glutathione S transferase protein, or a recombinant protein with multiple histidine residues. The expressed protein can be purified using a glutathione column or nickel column. Subsequently, if necessary, regions of the fusion protein (apart from the desired protein) can be digested and removed with thrombin or factor Xa, etc. The natural form of the protein of the invention can be isolated by, for example, purifying a cell extract containing the protein with an affinity column to which the antibody of the present invention described below is bound.

The present invention also includes partial peptides of the protein of the present invention. A partial peptide of the present invention comprises an amino acid sequence of at least seven amino acids, preferably eight or more amino acids, and more preferably nine or more amino acids. The partial peptide can be used for, for example, production of an antibody against the protein of the present invention, screening of compounds that bind to the present protein, screening of receptors of the present protein, or preparation of a competition inhibitor of the present protein. In addition, present invention includes partial peptides having, for example, the ability to bind to a receptor, but not the ability to activate the receptor (functioning as a competitive inhibitor of the protein of the present invention). Partial polypeptides of the present invention can be produced by genetic engineering techniques, known peptide synthesis methods, or by cleaving the protein of the present invention with a suitable peptidase.

Moreover, the present invention relates to DNA encoding the protein of the present invention. In addition to being used for the production of the protein of the present invention either in vivo or in vitro as previously mentioned, the DNA of the present invention may also be applied in, for example, gene therapy against diseases caused by aberrations of the gene encoding the protein of the present invention. Any type of DNA, such as cDNA synthesized from mRNA, genomic DNA, or synthetic DNA, can be used, so long as the DNA encodes the protein of the present invention. Also as long as they can encode the present protein, DNAs comprising arbitrary sequences based on the degeneracy of the genetic code are also included.

The DNA of the present invention can be prepared by using methods known in the art. For example, a cDNA library can be constructed from cells expressing the protein of the present invention and hybridization can be conducted using a part of the DNA sequence of the present invention (for example, DNA sequence shown in SEQ ID NO: 1) as a probe. Alternatively, the DNA of the present invention can be obtained by preparing RNA from cells expressing the protein of the present invention, synthesizing oligo-DNAs based on the DNA sequence of the present invention (for example, the DNA sequence shown in SEQ ID NO: 1), and amplifying the cDNA encoding the protein of the present invention by PCR using the oligonucleotides as primers.

The nucleotide sequence of the obtained cDNA is determined to find an open reading frame, and thereby the amino acid sequence of the protein of the invention can be obtained. The cDNA obtained may also be used as a probe for screening a genomic library to isolate genomic DNA.

More specifically, mRNAs may first be prepared from a cell, tissue, or organ (e.g., organs such as the lungs, liver, kidney, etc. or from an embryo) in which the protein of the invention is expressed. Known methods can be used to isolate mRNAs; for instance, total RNA is prepared by guanidine ultracentrifugation (Chirgwin et al., Biochemistry 18:5294–5299, 1979) or AGPC method (Chomczynski et al., Anal. Biochem. 162:156–159, 1987), and mRNA is purified from total RNA using an mRNA Purification Kit (Pharmacia), and such. Alternatively, mRNA may be directly purified by the QUICKPREP™ mRNA Purification Kit (Pharmacia).

The obtained mRNA is used to synthesize cDNA using reverse transcriptase. cDNA may be synthesized by using a kit such as the AMV Reverse Transcriptase First-strand cDNA Synthesis Kit (Seikagaku Kogyo). Alternatively, cDNA may be synthesized and amplified following the 5'-RACE method (Frohman et al., Proc. Natl. Acad. Sci. USA 85:8998–9002, 1988; Belyavsky et al., Nucleic Acids Res. 17:2919–2932, 1989), using the synthesized DNA as a primer, the 5'-AMPLI FINDER RACE™ Kit (Clontech), and polymerase chain reaction (PCR).

A desired DNA fragment is prepared from the PCR products and ligated with a vector DNA. The recombinant vectors are used to transform *E. coli* and such, and a desired recombinant vector is prepared from a selected colony. The nucleotide sequence of the desired DNA may be verified by conventional methods, such as dideoxynucleotide chain termination.

The DNA of the invention may be designed to have a nucleotide sequence having a high expression efficiency by taking into account the frequency of codon usage in the host used for the expression (Grantham et al., Nucleic Acids Res. 9:43–74, 1981). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of an initiation codon (ATG) and/or stop codon (TAA, TGA, or TAG).

Specifically, the DNA of the present invention includes a DNA comprising nucleotides from nucleotide A at position 87 to nucleotide T at position 752 of SEQ ID NO:1, and a DNA comprising nucleotides from nucleotide T at position 159 to nucleotide T at position 752 in the nucleotide sequence of SEQ ID NO:1.

The DNA of the present invention also includes a DNA that hybridizes to a DNA comprising the nucleotide sequence indicated in SEQ ID NO:1 under stringent conditions and is functionally equivalent to the protein described in SEQ ID NO:2. Examples of hybridization conditions include the conditions previously described. The hybridized DNA may preferably be naturally occurring DNA, such as cDNA or chromosomal DNA.

The DNA of the present invention can be used to produce the protein of the present invention as a recombinant protein. In addition, when there is a defect in the DNA encoding the protein of the present invention, the DNA of the present invention may also be applied to functional inhibition by an antisense, or gene therapy by substituting it with the normal gene.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1. In the case of an isolated nucleic acid molecule which is longer than or equivalent in length to the reference sequence, e.g., SEQ ID NO:1, the comparison is made with the full length of the reference sequence. Where the isolated nucleic acid molecule is shorter that the reference sequence, e.g., shorter than SEQ ID NO:1, the comparison is made to a segment of the reference sequence of the same length (excluding any loop required by the homology calculation).

As used herein, "% identity" of two amino acid sequences, or of two nucleic acid sequences, is determined using the algorithm of Karlin and Altschul (PNAS USA 87:2264–2268, 1990), modified as in Karlin and Altschul, PNAS USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score= 50, wordlength=3. To obtain gapped alignment for comparison purposes, GappedBLAST is utilized as described in Altschul et al (Nucleic Acids Res. 25:3389–3402, 1997). When utilizing BLAST and GappedBLAST programs the default parameters of the respective programs (e.g., XBLAST and NBLAST) are used to obtain nucleotide sequences homologous to a nucleic acid molecule of the invention.

The present invention also relates to a vector into which the DNA of the present invention is inserted. The vectors of the present invention are useful for carrying the DNA of the present invention and to express the protein of the present invention in a host cell.

When *E. coli* is used as the host cell, any vector can be used as long as it comprises an "ori", to amplify and mass-produce the vector in *E. coli* (e.g., JM109, DH5α, HB101, or XL1Blue), and a marker gene for selecting the transformed *E. coli* (e.g., a drug-resistant gene selected by a drug (e.g., ampicillin, tetracycline, kanamycin, or chloramphenicol). For example, M13-series vectors, pUG-series vectors, pBR322, pBluescript, pCR-Script, and such, can be used. Other than the vectors used above, pGEM-T, pDIRECT, pT7, and so on, can also be used for subcloning and excision of the cDNA. When using a vector to produce the protein of the present invention, an expression vector is especially useful. When, for example, the objective is to be expressed in *E. coli*, the expression vector should have the above characteristics in order to be amplified in *E. coli*. When *E. coli*, such as JM109, DH5α, HB101, or XL1 Blue, are used as the host cell, the vector should have a promoter, for example, lacZ promoter (Ward et al., Nature 341:544–546, 1989; FASEB J. 6:2422–2427, 1992), araB promoter (Better et al., Science 240:1041–1043, 1988), or T7 promoter, that can efficiently promote the expression of the desired gene in *E. coli*. Other examples of the vectors are pGEX-5X-1 (Pharmacia), QIAEXPRESS® system (Qiagen), pEGFP, and pET (for this vector, BL21, a strain expressing T7 RNA polymerase, is preferably used as the host).

In addition, a signal sequence for secreting a polypeptide may be contained in the vector. The pelB signal sequence (Lei et al., J. Bacteriol. 169:4379, 1987) can be used as the signal sequence for protein secretion when the secretory protein is produced into the periplasm of *E. coli*. Introduction of the vector into host cells can be carried out using, for example, the calcium chloride method, electroporation, and so forth.

Examples of vectors used for producing the protein of the invention other than those derived from *E. coli* include, for example, expression vectors derived from mammals (e.g., pcDNA3 (Invitrogen), pEGF-BOS (Nucleic Acids. Res. 18(17):5322, 1990), pEF, and pCDM8), those derived from insect cells (e.g., the "Bac-to-BAC baculovirus expression system" (GIBCO BRL) and pBacPAK8), those derived from plants (e.g., pMH1 and pMH2), those derived from animal viruses (e.g., pHSV, pMV, and pAdexLcw), those derived from retroviruses (e.g., pZIpneo), those derived from yeast (e.g., "Pichia Expression Kit" (Invitrogen), pNV11, and SP-Q01), and those derived from *Bacillus subtilis* (e.g., pPL608 and pKTH50).

For expression in animal cells such as CHO cells, COS cells, or NIH3T3 cells, it is essential for the vector to have a promoter necessary for expression in the cells, such as the SV40 promoter (Mulligan et al., Nature 277:108, 1979), MMLV-LTR promoter, EF1α promoter (Mizushima et al., Nucleic Acids Res. 18:5322, 1990), and CMV promoter. More preferably, such a vector comprises a gene for selecting cell transformation (for example, a drug-resistant gene that allows selection by a drug (such as neomycin or G418). Examples of vectors having such characteristics include, for example, pMAM, pDR2, pBK-RSV, pBK-CMV, pOPRSV, and pOP13.

Moreover, for stably expressing a gene and amplifying the number of copies of the gene within cells, one example of a method that can be used is the method in which a vector (such as PCH01) having a DHFR gene that compensates for a defect in the nucleic acid synthesis pathway is inserted into CHO cells, which is followed by amplification by methotrexate (MTX). For transient gene expression, an example method is one in which COS cells, having a gene on their chromosomes that expresses SV40 T antigen, are transformed with a vector (such as pcD) having an SV40 replication origin. Replication origins derived from polioma virus, adenovirus, bovine papillomavirus (BPV), and so forth can be also used. Moreover, in order to amplify the number of gene copies in a host cell line, the expression vector can contain aminoglycoside transferase (APH) gene, thymidine kinase (TK) gene, *E. coli* xanthine guanine phosphoribosyl transferase (Ecogpt) gene, dihydrofolic acid reductase (dhfr) gene, and so forth, as a selective marker.

On the other hand, for expressing the DNA of the present invention in the living body of animals, a method in which the DNA is first incorporated into a suitable vector, and then the vector is introduced into the living body by the retrovirus method, liposome method, cationic liposome method, adenovirus method, and so forth, may be used. Thereby, gene therapy can be carried out against diseases caused by a mutation in the gene that encodes the protein of the present invention. For example, without limitation, adenovirus vectors (e.g., pAdexlcw) and retrovirus vectors (e.g., pZIPneo) are used as vectors. General gene manipulation techniques such as the insertion of the DNA of the present invention into a vector can be carried out in accordance with ordinary methods (Molecular Cloning, 5.61–5.63). Administration into the living body may be carried out by either the ex vivo method or in vivo method.

Furthermore, the present invention relates to a host cell into which the vector of the present invention has been introduced. There are no particular restrictions on the host cell, and includes, for example, *E. coli* and various animal cells. The host cell of the present invention can be used, for example, as a production system for the production and expression of the protein of the present invention. Production systems for producing the protein include both in vitro and in vivo systems. Examples of in vitro production systems include those using eukaryotic cells or prokaryotic cells.

When using eukaryotic cells, for example, animal cells, plant cells, and fungal cells can be used as the host. Known examples of animal cells include mammalian cells such as CHO (J. Exp. Med. 108:945, 1995), COS, 3T3, myeloma, BHK (baby hamster kidney), HeLa, and Vero, amphibian cells such as Xenopus oocytes (Valle et al., Nature 291:358–340, 1981), and insect cells such as sf9, sf21, and Tn5. Particularly preferable CHO cells are those deficient in the DHFR gene, dhfr-CHO (Proc. Natl. Acad. Sci. USA 77:4216–4220, 1980) and CHO K-1 (Proc. Natl. Acad. Sci. USA 60:1275, 1968). For mass expression in animal cells, CHO cells are particularly preferable. A vector can be introduced into host cells by, for example, the calcium phosphate method, DEAE dextran method, method using cationic ribosome DOTAP (Boehringer-Mannheim), electroporation, and lipofection.

Known examples of plant cells used as protein production systems include cells derived from *Nicotiana tabacum*, and these cells can be cultured as a callus culture. Yeasts such as *Saccharomyces* species, e.g., *Saccharomyces cerevisiae*, as well as filamentous bacteria such as *Aspergillus* species, e.g., *Aspergillus niger* are known as fungal cells.

For prokaryotic cells, bacterial cells can be used as the production system. Examples of bacterial cells include *E. coli* such as *E. coli* JM109, DH5a and HB101, as well as *Bacillus subtilis*.

These cells are transformed by desired DNA, and the resulting transformants are cultured in vitro to obtain the protein. Transformants can be cultured using known methods. Culture medium such as DMEM, MEM, RPMI1640, or IMDM may be used for animal cells with or without serum supplements such as fetal calf serum (FCS). The pH of the culture medium is preferably between about 6 and 8. Such cells are typically cultured at about 30 to 40° C. for about 15 to 200 hr, and the culture medium may be replaced, aerated, or stirred as necessary.

Animal and plant hosts may be used for in vivo protein-producing systems . For example, a desired DNA can be introduced into an animal or plant host. Encoded proteins are produced in vivo, and then recovered. These animal and plant hosts are included in the host cells of the present invention.

Animals to be used for the production systems described above include, but are not limited to, mammals and insects. Mammals such as goats, pigs, sheep, mice, and cattle may be used (Vicki Glaser, SPECTRUM Biotechnology Applications, 1993). Alternatively, the mammals may be transgenic animals.

For instance, a desired DNA may be prepared as a fusion gene by fusing it with a gene that encodes a protein specifically produced into milk, such as goat β casein gene. DNA fragments comprising the fusion gene are injected into goat embryos, which are then introduced back into female goats. Proteins of interest can be recovered from milk produced by the transgenic goats (i.e., those born from the goats that had received the modified embryos) or from their offspring. To increase the amount of milk containing the proteins produced by transgenic goats, appropriate hormones may be administered (Ebert et al., Bio/Technology 12:699–702, 1994).

Alternatively, insects, such as the silkworm, may be used. A DNA encoding the desired protein inserted into a baculovirus can be used to infect silkworms, and the desired protein can be recovered from their body fluids (Susumu et al., Nature 315:592–594, 1985).

As plants, for example, tobacco can be used. When using tobacco, DNA encoding the desired protein may be inserted into a plant expression vector, such as pMON530, which is introduced into bacteria, such as *Agrobacterium tumefaciens*. Then the bacteria is used to infect tobacco, such as *Nicotiana tabacum*, and a desired polypeptide is recovered from their leaves (Julian et al., Eur. J. Immunol. 24:131–138, 1994).

A protein of the present invention obtained as above may be isolated from the inside or outside (such as the culture medium) of the host cell, and purified as a substantially pure homogeneous protein. The method for protein isolation and purification is not limited to any specific method; in fact, any standard method may be used. For instance, column chromatography, filters, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

For chromatography, for example, affinity chromatography, ion-exchange chromatography, hydrophobic chromatography, gel filtration, reverse phase chromatography, adsorption chromatography, and such may be used (Strategies for Protein Purification and Characterization: A Laboratory Course Manual. Ed. Daniel R. Marshak et al., Cold Spring Harbor Laboratory Press, 1996). These chromatographies may be performed by liquid chromatography such as HPLC and FPLC. Thus, the present invention provides highly purified proteins produced by the above methods.

A protein of the present invention may be arbitrarily modified or peptides may be partially deleted by treating it with an appropriate protein modification enzyme before or after purification. Useful protein modification enzymes include, but are not limited to, trypsin, chymotrypsin, lysylendopeptidase, protein kinase, glucosidase and such.

The present invention also relates to an antibody that binds to the protein of the invention. An antibody of the invention may take any form, including monoclonal antibodies, as well as polyclonal antibodies. Furthermore, antiserum obtained by immunizing an animal such as a rabbit, or the like, with the protein of the invention, all classes of polyclonal and monoclonal antibodies, human antibodies, and humanized antibodies produced by genetic recombination are included.

A protein of the invention used as an antigen to obtain an antibody may be derived from any animal species, but preferably it is from a mammal such as a human, mouse, or rat, more preferably from a human. A human-derived protein may be obtained from the nucleotide or amino acid sequences disclosed herein.

A whole protein or a partial peptide of a protein may be used as a sensitizing antigen in the present invention. A partial peptide may be, for example, an amino (N)-terminal or carboxy (C)-terminal fragment of a protein. Herein, an "antibody" is defined as an antibody that specifically reacts with either the full length or a fragment of a protein.

A gene encoding the protein of the invention or a its fragment may be inserted into a known expression vector, a host cell as described herein may be transformed with the vector, and the desired protein or its fragment for use as a sensitizing antigen may be obtained from the outside or inside of host cells by any standard method. Alternatively, cells expressing the protein or their lysates, or a chemically synthesized protein may be used as the antigen.

Any mammal may be immunized with the antigen, but preferably the compatibility with parental cells used for cell fusion is taken into account. In general, animals of Rodentia, Lagomorpha, or Primates are used.

Animals of Rodentia include, for example, mice, rats, and hamsters. Animals of Lagomorpha include, for example, rabbits. Animals of Primates include, for example, monkeys of Catarrhini (old world monkey) such as *Macaca fascicularis*, rhesus monkeys, sacred baboons, or chimpanzees.

Methods for immunizing animals with antigens are known in the art. In a standard method, a sensitizing antigen is injected intraperitoneally or subcutaneously to mammals. More specifically, an appropriate amount of a standard adjuvant, such as Freund's complete adjuvant, is mixed with the sensitizing antigen, diluted and suspended in an appropriate amount of phosphate buffered saline (PBS), physiological saline, or such, emulsified, and then administered to mammals. Preferably, this is followed by several administrations of antigen mixed with an appropriately amount of Freund's incomplete adjuvant every 4 to 21 days. An appropriate carrier may also be used for immunization of sensitizing antigens. After an immunization as above, the serum is examined for an increase of the amount of desired antibodies by a standard method.

Polyclonal antibodies against the protein of the present invention may be prepared by collecting blood from the immunized mammal examined for an increase of desired antibodies in the serum, and by separating serum from the blood by any conventional method. Polyclonal antibodies may be used as serum containing polyclonal antibodies, or if necessary, a fraction containing the polyclonal antibodies may be isolated from the serum for use. For example, immunoglobulin G or M can be prepared by using an affinity column coupled with the protein of the present invention to obtain a fraction that recognizes only the protein, followed by purifying this fraction using a protein A column or protein G column.

To prepare a monoclonal antibody, immune cells are collected from the mammal sensitized with the above antigen after verifying that the desired antibody level has increased in the serum. The cells are then subjected to cell fusion. The immune cells used for cell fusion are preferably obtained from spleen. The other parent cell that is fused with the above immune cell is preferably a mammalian myeloma cell, and more preferably a myeloma cell that has acquired a special feature that can be used for the selection of fusion cells by a drug.

Cell fusion of the above immune cell and myeloma cell may be performed by any standard method, such as those described in literature (Galfre et al., Methods Enzymol. 73:3–46, 1981).

Resulting hybridomas obtained by cell fusion may be selected by cultivating them in a standard selection medium, such as HAT medium (hypoxanthine, aminopterin, and thymidine containing medium). The cell culture is typically continued in the HAT medium until all cells other than the desired hybridoma (non-fused cells) die, usually from several days to several weeks. Then, the standard limiting dilution is performed to screen and clone a hybridoma cell producing the desired antibody.

Besides the above method in which a nonhuman animal is immunized with an antigen for preparing hybridoma, human lymphocytes such as those infected by the EB virus may be immunized with a protein, protein expressing cells, or their lysates in vitro. Then, the immunized lymphocytes are fused with human-derived myeloma cells capable of indefinite division, such as U266, to yield a hybridoma producing a desired human antibody capable of binding to the protein (Unexamined Published Japanese Patent Application (JP-A) No. Sho 63-17688).

Subsequently, the hybridomas thus obtained are transplanted into the abdominal cavity of a mouse from which the ascites is collected. The monoclonal antibodies thus obtained can be purified by, for example, ammonium sulfate precipitation or by column chromatography using a protein A or protein G column, a DEAE ion exchange column, an affinity column, and such to which the protein of the invention is coupled. The antibody of the invention can be used not only for purifying and detecting a protein of the invention, but also as a candidate for an agonist or antagonist to a protein of the present invention. The antibody is also expected to be used in antibody therapy against diseases related to the present protein. When using the resulting antibody for the purpose of administration to the human body (antibody therapy), human antibodies or humanized antibodies are preferred to reduce immunogenicity.

For example, human antibodies against a protein can be obtained using hybridomas obtained by fusing myelomas with antibody-producing cells, which are obtained by immunizing transgenic animals having the human antibody gene repertoire with an antigenic protein, cells expressing the protein, or a lysate thereof (See WO92-03918, WO93-2227, WO94-02602, WO94-25585, WO96-33735 and WO96-34096).

Alternatively, an immune cell, such as an immunized lymphocyte, which produces antibodies may be immortalized by an oncogene and used for preparing monoclonal antibodies.

Monoclonal antibodies thus obtained can be also be recombinantly prepared using conventional genetic engineering techniques (see, for example, Borrebaeck C. A. K. and Larrick J. W. Therapeutic Monoclonal Antibodies, published in the United Kingdom by MacMillan Publishers LTD, 1990). A recombinant antibody can be produced by cloning a DNA encoding the antibody from an immune cell such as a hybridoma or an immunized lymphocyte producing the antibody, inserting this DNA into an appropriate vector, and introducing this into a host cell. The present invention also provides recombinant antibodies prepared as described above.

An antibody of the present invention may be a fragment of an antibody or a modified antibody, so long as it binds to one or more of the proteins of the invention. For instance, the antibody fragment may be Fab, F (ab')$_2$, Fv, or single chain Fv (scFv), in which Fv fragments from H and L chains are ligated by an appropriate linker (Huston et al., Proc. Natl. Acad. Sci. USA 85:5879–5883, 1988). More specifically, an antibody fragment may be generated by treating an antibody with an enzyme such as papain or pepsin. Alternatively, a gene encoding the antibody fragment may be constructed, inserted into an expression vector, and expressed in an appropriate host cell (see, for example, Co et al., J. Immunol. 152:2968–2976, 1994; Better et al., Methods Enzymol. 178:476–496, 1989; Pluckthun et al., Methods Enzymol. 178:497–515, 1989; Lamoyi, Methods Enzymol. 121:652–663, 1986; Rousseaux et al., Methods Enzymol. 121:663–669, 1986; Bird et al., Trends Biotechnol. 9:132–137, 1991).

An antibody may be modified by conjugation with a variety of molecules, such as polyethylene glycol (PEG). The present invention encompasses such modified antibodies. A modified antibody can be obtained by chemically modifying an antibody. These modification methods are conventional in the field.

An antibody of the present invention may be obtained as a chimeric antibody comprising a variable region derived from a nonhuman antibody and the constant region derived from a human antibody. Alternatively, the present antibody may be obtained as a humanized antibody, comprising the complementarity-determining region (CDR) derived from a nonhuman antibody, the framework region (FR) constant region derived from a human antibody. Such antibodies can be prepared by using known techniques.

An Antibody obtained as above may be purified to homogeneity. Methods generally used for separating and purifying ordinary proteins may be used for separating and purifying the present antibody. For example, the antibody can be separated and/or purified by the appropriate selection and combined use of column chromatographies such as affinity chromatography and the like, filters, ultrafiltration, salting-out, dialysis, SDS polyacrylamide gel electrophoresis, isoelectric focusing, etc. (Antibodies: A Laboratory Manual. Ed Harlow and David Lane, Cold Spring Harbor Laboratory, 1988), without limitation. The concentration of the antibody obtained as above may be determined by measuring the absorbance or by an enzyme-linked immunosorbent assay (ELISA), and such.

A column used in affinity chromatography is exemplified by protein A column or protein G column. For example, protein A column includes HYPER D™, POROS™, and SEPHAROSE™ F. F. (Pharmacia).

In addition to affinity chromatography, the chromatography method includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographies can be carried out by liquid-phase chromatography such as HPLC, FPLC, or the like.

For example, the determination of absorbance, Enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody, which recognizes the primary antibody and which is labeled with an enzyme such as alkaline phosphatase, is applied, and the plate is incubated. After washing, an enzyme substrate, such as p-nitrophenyl phosphate, is added to the plate, and the absorbance is measured to evaluate the antigen binding activity of the sample. A fragment of the protein, such as a C-terminal or N-terminal fragment, may also be used. BIA-CORE® (Pharmacia) may be used to evaluate the activity of the antibody according to the present invention.

The above methods allow the detection or measurement of the protein of the invention, by exposing the antibody of the invention to a sample presumed to contain the protein of the invention, and detecting or measuring the immune complex formed by the antibody and the protein.

Because the method of detection or measurement of the protein according to the invention can specifically detect or measure a protein, the method may be useful in a variety of experiments in which the protein is used.

The present invention also relates to a nucleotide comprising at least 15 nucleotides that hybridizes to the DNA (SEQ ID NO:1) encoding the protein described in SEQ ID NO:2 or to a complementary strand thereof. Nucleotides of the present invention specifically hybridize to DNA (SEQ ID NO:1) encoding the protein described in SEQ ID NO:2 or to a complementary strand thereof. Here, the term "specifically hybridize" refers to the absence of significant cross-hybridization with DNA encoding other proteins under normal hybridization conditions, and preferably under stringent hybridization conditions. Such nucleotides include probes, primers, nucleotides, and nucleotide derivatives (e.g., DNA encoding antisense oligonucleotides and ribozyme) that are able to specifically hybridize to DNA encoding the protein of the present invention or to complementary DNA thereof. In addition, such nucleotides can also be used for the production of DNA chips.

The present invention comprises, for example, an antisense oligonucleotide that hybridizes to any part of the nucleotide sequence of SEQ ID NO:1. The antisense oligonucleotide is preferably an antisense of a continuous sequence comprising at least 15 nucleotides or more within the nucleotide sequence SEQ ID NO:1. More preferably, the above continuous sequence comprising at least 15 nucleotides or more that contains a translation initiation codon.

A derivative or modified form of an antisense oligonucleotide may also be used. The latter form may be modified with lower alkylphosphonate such as methylphosphonate or ethylphosphonate, or with phosphorothioate, or phosphoroamidate.

Herein, an antisense oligonucleotide is not restricted to one in which all nucleotides are complementary to the corresponding nucleotides within a given region of a DNA or mRNA, as long as it can specifically hybridize to the nucleotide sequence of SEQ ID NO:1, it may have one or more nucleotide mismatches.

Such nucleotides have a homology of at least 70%, preferably 80% or more, more preferably 90% or more, and even more preferably 95% or more within a continuous sequence comprising at least 15 nucleotides or more. To determine the degree of homology, the algorithm described herein may be used. As described in the following Examples, the above DNA is useful as a probe for detecting or isolating a DNA encoding the protein of the invention, or as a primer for its amplification.

A derivative of an antisense oligonucleotide of a present invention may act on cells producing the protein of the invention and bind to a DNA or mRNA encoding the protein, and then, it may inhibit the expression of the protein of the invention by inhibiting its transcription or translation, or by promoting the degradation of mRNA, and thereby inhibiting the function of the protein of the invention.

A derivative of an antisense oligonucleotide of the present invention may be mixed with an appropriate nucleotide that is inactive against the derivative, and used as a medicine for external application, such as an ointment or poultice.

If necessary, it may be mixed with an excipient, isotonizing agent, solubilizing agent, stabilizer, preservative, painkiller, or the like, and prepared as a tablet, powder, granule, capsule, liposome capsule, injectable solution, liquid formulation, nose drops, freeze-dried agent, etc. The above may be achieved according to standard methods.

For treating patients, a derivative of an antisense oligonucleotide of the present invention may be, for example, directly applied to the affected area of a patient, or administered into blood vessels so as to finally reach the affected area. Moreover, the derivative may be encapsulated in antisense-encapsulating materials such as liposomes, poly-L-lysine, lipid, cholesterol, lipofectin, or their derivatives in order to increase durability and/or membrane permeability.

Dose of the derivative of the antisense oligonucleotide of the present invention may be appropriately adjusted depending on the patient's condition, and an appropriate amount such as 0.1 to 100 mg/kg, or more preferably 0.1 to 50 mg/kg may be administered.

As an antisense oligonucleotide of the present invention inhibits expression of the protein of the invention, it can be utilized as an inhibitor of a biological activity of the protein of the invention. An inhibitor of expression comprising an antisense oligonucleotide of the present invention is useful because it can inhibit the a biological activity of the protein of the invention.

Further, the present invention relates to a method for screening compounds that bind to the protein of the present invention using the protein, as well as compounds which can be isolated by the screening method (e.g., receptors, agonists, and antagonists).

The protein of the present invention used for screening may be a recombinant protein, natural protein, or a partial peptide. One embodiment of this screening method comprises the steps of (a) contacting a test sample with the protein of the present invention or its partial peptide, and (b) selecting a compound having an activity for binding to the protein or its partial peptide. Without limitation, the test sample includes cell extracts, cell culture supernatants, products of fermentation microorganisms, marine organism extracts, plant extracts, purified or crude proteins, peptides, non-peptide compounds, synthetic low molecular weight compounds, and naturally-occurring compounds. The protein of the present invention can be contacted with the test sample in the form of, for example, a purified protein, solubilized protein, a protein bound to a carrier, a fusion protein with another protein, a protein expressed on a cell membrane, or as a membrane fraction.

Numerous methods known to those skilled in the art can be used as methods for screening a protein that binds to the protein of the present invention using the protein. Such screenings can be carried out, for example, by the immunoprecipitation method. Specifically, the method can be carried out as follows. The gene encoding the protein of this invention is expressed by inserting the gene downstream of a promoter for expressing a foreign gene, such as pSV2neo, pcDNA I, pCD8, etc., and expressing the gene in animal cells, etc. Any generally used promoter may be employed for the expression, including the SV40 early promoter (Rigby In Williamson (ed.), Genetic Engineering, vol. 3. Academic Press, London, p. 83–141, 1982), EF-1α promoter (Kim et al., Gene 91:217–223, 1990), CAG promoter (Niwa et al., Gene 108:193–200, 1991), RSV LTR promoter (Cullen, Methods in Enzymol. 152:684–704, 1987), SRα promoter (Takebe et al., Mol. Cell. Biol. 8:466, 1988), CMV immediate early promoter (Seed et al., Proc. Natl. Acad. Sci. USA 84:3365–3369, 1987), SV40 late promoter (Gheysen et al., J. Mol. Appl. Genet. 1:385–394, 1982), Adenovirus late promoter (Kaufman et al., Mol. Cell. Biol. 9:946, 1989), HSV TK promoter, etc. Transfer of a foreign gene into animal cells for expression can be performed by any one of the following methods, including the electroporation method (Chu et al., Nucl. Acid Res. 15:1311–1326, 1987), the calcium phosphate method (Chen et al., Mol. Cell. Biol. 7:2745–2752, 1987), the DEAE dextran method (Lopata et al., Nucl. Acids Res. 12:5707–5717, 1984; Sussman et al., Mol. Cell. Biol. 4:1642–1643, 1985), the lipofectin method (Derijard, Cell 7:1025–1037, 1994; Lamb et al., Nature Genetics 5:22–30, 1993; Rabindran et al., Science 259:230–234, 1993), etc. The protein of this invention can be expressed as a fusion protein having a recognition site for a monoclonal antibody by introducing such a site the specificity of which has been established, into the N- or C-terminal of the protein of this invention. For this purpose, a commercial epitope-antibody system can be utilized (Jikken Igaku, Exp. Med. 13:85–90, 1995). Vectors are commercially available which are capable of expressing fusion proteins with β-galactosidase, maltose-binding protein, glutathione S-transferase, green fluorescence protein (GFP), and such, via a multi-cloning site.

To minimize the alteration in properties of the protein of this invention due to fusion protein formation, a method for preparing a fusion protein by introducing only a small epitope portion comprising several to ten amino acid residues has been reported. For example, the epitopes of polyhistidine (His-tag), influenza hemagglutinin (HA), human c-myc, FLAG, Vesicular stomatitis virus glycoprotein (VSV-GP), T7 gene 10 protein (T7-tag), human herpes simplex virus glycoprotein (HSV-tag), E-tag (epitope on the monoclonal phage), and such, and monoclonal antibodies that recognize these epitopes can be utilized as epitope-antibody systems for screening proteins binding to the protein of this invention (Jikken Igaku, Exp. Med. 13:85–90, 1995).

In immunoprecipitation, immune complexes are formed by adding these antibodies to a cell lysate prepared using suitable surfactants. This immune complex comprises the protein of this invention, a protein capable of binding to the protein, and an antibody. Immunoprecipitation can also be performed using an antibody against the protein of this invention besides antibodies to the above-described epitopes. An antibody to the protein of this invention can be prepared by inserting a gene encoding the protein of this invention into an appropriate expression vector of E. coli to express it in the bacterium, purifying the protein thus expressed, and immunizing rabbits, mice, rats, goats, chicken, and such, with the purified protein. The antibody can also be prepared by immunizing the above-described animals with a partial peptide of the protein of this invention.

Immune complexes can be precipitated using, for example, Protein A Sepharose and Protein G Sepharose when the antibody is a murine IgG antibody. In addition, in the case where the protein of this invention is prepared as a fusion protein with an epitope of, for example, GST, and such, the immune complex can be formed using a substance that specifically binds to this epitope, such as glutathione-Sepharose 4B, and such, giving the same result as in the case where the antibody for the protein of this invention is used.

Immunoprecipitation, in general, may be carried out according to, or following the method described in literature (Harlow et al.: Antibodies, pp. 511–552, Cold Spring Harbor Laboratory publications, New York, 1988).

SDS-PAGE is generally used for the analysis of immunoprecipitated proteins. Bound proteins can be analyzed based on the molecular weights of proteins using a gel of an appropriate concentration. In this case, although proteins bound to the protein of this invention, in general, are hardly detectable by the usual protein staining methods, such as Coomassie staining and silver staining, the detection sensitivity can be improved by culturing cells in a medium containing radio isotope-labeled $^{35}$S-methionine and $^{35}$S-cysteine to label proteins inside the cells, and detecting the labeled proteins. Once the molecular weight of the protein is determined, the desired protein can be purified directly from SDS-polyacrylamide gel and sequenced.

In addition, for example, West Western blotting method (Skolnik et al., Cell 65:83–90, 1991) can be used to isolate a protein that binds to the protein of the present invention using the protein. Namely, a cDNA library is prepared using a phage vector (such as λgt11 or ZAP) from cells, tissue, or organs (such as the heart, lung, liver, kidney, and so forth, and embryos) in which a protein that binds to the protein of the present invention is presumed to be expressed, and then, this cDNA library is expressed on LB-agarose, . The expressed protein is fixed on a filter and the fixed protein is purified, the labeled protein of the present invention is reacted with the above filter, and plagues that express a protein bound to the protein of the present invention is detected using the label. Methods for labeling a protein of the present invention include those that use the binding properties of biotin and avidin, those that use antibodies that specifically bind to the protein of the present invention or a peptide or polypeptide (such as GST) that has been fused with the protein, those that use radioisotopes or fluorescence In addition, other embodiments of the screening method of the present invention include methods that use a two-hybrid system using cells (such as the "MATCHMAKER™ Two-Hybrid System", "Mammalian MATCHMAKER™ Two-Hybrid Assay Kit", and "MATCHMAKER™ One-Hybrid System" (all by Clontech), the "HYBRIZAP™ Two-Hybrid Vector System" (Stratagene), and the "CYTO TRAP™ two-hybrid system" (Stratagene); References: Dalton et al., Cell 68:597–612, 1992; Fields et al., Trends. Genet. 10:286–292, 1994).

In a two-hybrid system, a cDNA library is prepared from cells in which protein that bind to the protein of the present invention is presumed to be expressed by expressing the protein of the present invention in yeast cells by fusing it with the SRF DNA binding region or GAL4 DNA binding region, and expressing in a form that fuses with the VP16 or GAL4 transcriptional activation region. This cDNA library is then introduced into the above yeast cells, and library-derived cDNA is isolated from the positive clones detected (when a protein that binds to the protein of the present invention is expressed in yeast cells, a reporter gene is activated by their binding, thereby making it possible to confirm the positive clones). Protein corresponding to the isolated cDNA can then be obtained by introducing said cDNA into *E. coli* and expressing it therein.

Examples of reporter genes that can be used include HIS3 gene, Ade2 gene, LacZ gene, CAT gene, luciferase gene and PAI-1 (plasminogen activator inhibitor type 1) gene.

Screening of compounds that bind to the protein of the present invention can be carried out using affinity chromatography. For example, the protein of the present invention is immobilized on a carrier of an affinity column, and then a test sample presumed to express a protein that binds to the protein of the present invention is applied to the column. In this case, for example, cell extracts and cell lysates can be used as test samples. After applying the test sample, the protein that binds to the protein of the present invention can be prepared by washing the column.

DNA encoding the resulting protein can be obtained by analyzing the amino acid sequence of the protein, synthesizing oligo DNA based on that sequence, and screening a cDNA library by using the DNA as a probe.

In the present invention, a biosensor utilizing the surface plasmon resonance phenomena can be used as means for detecting or determining bound compounds. Biosensors using surface plasmon resonance phenomena allow real-time observation of the interaction between the protein of the present invention and a test compound as a surface plasmon resonance signal using a trace amount of the protein and without labeling (for example, BIACORE® (Pharmacia)). Thus, using a BIACORE® or other biosensor allows one to evaluate the binding between the protein of the present invention and a test compound.

In addition, examples of methods known to persons skilled in the art for isolating compounds (including agonists and antagonists) that bind to the protein of the present invention without being limited to proteins, include: a method for screening molecules that bind to the protein of the present invention by allowing a synthetic compound, natural substance bank, or random phage peptide display library to act on an immobilized protein of the present invention; and a high-throughput screening method using combinatorial chemistry technology (Wrighton et al., Science 273:458–464, 1996; Verdine, Nature 384:11–13, 1996; Hogan, Jr., Nature 384:17–19, 1996).

Compounds that can be isolated by the screening can be drug candidates for promoting or inhibiting the activity of the protein of the present invention, and can be applied to the treatment of diseases caused by expression or functional abnormalities of the protein of the invention. A substance in which a portion of the structure of a compound, which has an activity for binding to the protein of the present invention and which was obtained by using the screening method of the present invention, is altered by addition, deletion, and/or substitution is also included in the compounds obtained by using the screening method of the present invention.

When using the compound obtained by the screening method of this invention and present protein as a drug for humans and mammals, for example, mice, rats, guinea pigs, rabbits, chicken, cats, dogs, sheep, pigs, cattle, monkeys, sacred baboons, and chimpanzees, the isolated compound itself can be directly administered to a patient, or it can be given after formulation by using commonly known pharmaceutical preparation methods. For example, according to the need, the drug can be taken orally as sugarcoated tablets, capsules, elixirs, and microcapsules, or parenterally in the form of injections of aseptic solutions or suspensions with water or any other pharmaceutically acceptable liquid. The compound may be formulated by mixing with, for example, pharmacologically acceptable carriers or media, specifically, sterilized water, physiological saline, plant oils, emulsifiers, suspending agents, surfactants, stabilizers, flavoring agents, excipients, vehicles, preservatives, binders, and so on, in a unit dose form required for generally accepted drug implementation. The amount of active ingredients in these preparations makes a suitable dosage within the indicated range acquirable.

Examples for additives which can be mixed with tablets and capsules are, binders such as gelatin, corn starch, tragacanth gum, and arabic gum; excipients such as crystalline cellulose; swelling agents such as corn starch, gelatin, and alginic acid; lubricators such as magnesium stearate; sweeteners such as sucrose, lactose, or saccharin; and flavoring agents such as peppermint, Gaultheria adenothrix oil, and cherry. When the unit dosage form is a capsule, a liquid carrier, such as oil, can also be included in the above ingredients. Sterile compositions for injections can be formulated following normal drug implementations using vehicles such as distilled water used for injections.

Physiological saline and isotonic liquids including glucose or other adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as polysorbate 80 (TM) and HCO-50.

Sesame oil or soy-bean oil can be used as a oleaginous liquid and may be used in conjunction with benzyl benzoate or benzyl alcohol as a solubilizer; may be formulated with a buffer such as phosphate buffer and sodium acetate buffer; a pain-killer such as procaine hydrochloride; a stabilizer such as benzyl alcohol and phenol; or an anti-oxidant. The prepared injection is filled into a suitable ampule.

The administration to patients is done by methods commonly known to those skilled in the art, such as by intra-arterial, intravenous, or subcutaneous injections, and in addition, as intranasal, bronchial, intramuscular, percutaneous, or oral administrations. One skilled in the art can suitably select the dosage according to the body-weight or age of a patient, or the method of administration. Also, if the compound can be encoded by DNA, the compound can be used for gene therapy by integrating the DNA into a vector for gene therapy. Although the dosage amount and method of administration differ according to the body-weight, age, and symptoms of a patient, one skilled in the art can suitably select these.

For example, although the dosage for a single administration of the protein of the present invention varies depending on the administration target, target organ, symptoms, administration method, and so forth, the dosage in the form of, for example, an injection preparation is usually considered to be in the range of about 100 μg to 20 mg per day for an adult (assuming the body weight is 60 kg).

For example, although the dosage of a compound that binds to the protein of the present invention or the dosage of a compound that inhibits the activity of the protein of the present invention varies according to the symptoms, in the case of oral administration, the dosage for an adult (assuming the body weight is 60 kg) is typically in the range of about 0.1 to 100 mg, preferably about 1.0 to 50 mg, and more preferably about 1.0 to 20 mg, per day.

In the case of parenteral administration, although the dosage for a single administration also varies according to the administration target, target organ, symptoms, and administration method, the dosage in the form of, for example, an injection preparation for an adult (assuming the body weight is 60 kg) is usually in the range of about 0.01 to 30 mg, preferably about 0.1 to 20 mg, and more preferably about 0.1 to 10 mg, per day for a convenient intravenous administration. In the case of other animals as well, it is possible to administer an amount converted to 60 kg of body weight or per area of body surface.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows the homology between the amino acid sequences encoded by clone 106 (above; SEQ ID NO:2) and *Drosophila* twisted gastrulation (TSG) gene (below; SEQ ID NO:5). Asterisks (*) indicate identical amino acid sequences, while dots (.) indicate similar amino acid sequences. Gaps are supplemented with bars.

All publications and patents cited herein are incorporated by reference in their entirety.

DETAILED DESCRIPTION

The present invention is described below in detail using examples, but it is not to be construed as being limited thereto.

EXAMPLE 1

Isolation of Clone 106

The AGM region was sampled from 11.5-day mice embryos, and polyA(+) RNA was prepared using FAST TRACK® (Invitrogen). Double-strand cDNA was synthesized using a random primer of the SUPERSCRIPT™ Choice System (GIBCO BRL). BstXI adapter (Invitrogen) was added after blunting the ends of the cDNA, and then 400 bp or longer cDNA were fractionated using the SizeSep 400 Spun Column (Pharmacia)

After the cDNA was mixed with pMXGM(-)v-mpLM2 (see Japanese Patent Application No. Hei 9-324912), which had been treated with BstX1 (TAKARA) beforehand, it was ligated using T4 DNA ligase. The resulting DNA was introduced into *E. coli* DH10B (GIBCO BRL) by electroporation using GENE PULSER® (BioRad), and cultured overnight. The cDNA library was purified using the JETSTAR™ column (GENOMED)

Packaging cells BOSC23 (Proc. Natl. Acad. Sci. USA 90:8392–8396, 1993) were transfected with the eDNA library using LIPOFECTAMINE™ (LIFE TECHNOLOGIES) BOSC23 were seeded into a 6-cm dish with DMEM (LIFE TECHNOLOGIES) containing 10% fetal calf serum (FOS, JRH BIOSCIENCES), and then washed with DMEM 16 hours later. 18 µl of LIPOFECTAMINE™ diluted beforehand with 200 µl of DMEM and 3 µg of the cDNA library diluted with 200 µl of DMEM were mixed together. This was kept standing at room temperature for 15 minutes, then 1.6 ml of DMEM was added thereto, and the mixture was added to the cells. After five hours, 2 ml of DMEM containing 20% FCS was added to the mixture and cultured for 19 hours. Subsequently, the medium was replaced with 3 ml of DMEM containing 10% FCS and the culture supernatant was collected 24 hours later. Mouse interleukin-3 (IL-3) and 10 µg/ml of hexadimethrine bromide were added to the culture supernatant containing the recombinant virus, and Ba/F3 were suspended for infection. 24 hours after the infection, the cells were washed three times with PBS, and further cultured with RPMI1640 (LIFE TECHNOLOGIES) containing 10% FCS. DNA was extracted from clones that proliferated in the absence of IL-3 and amplified by PCR using primers 5'-gggggTggACCATCCTCTA-3' (SEQ ID NO:3) and 5'-CgCgCAgCTgTAAACggTAg-3' (SEQ ID NO:4), designed to surround the cDNA insertion site, followed by recovery of the cDNA fragment. PCR was performed under the following conditions with the GENEAMP® PCR System 2400 (Applied Biosystems) using 50 µl of the reaction mixture containing 500 ng of DNA, 500 pM each of primer, 2.5 units of TAKARA LA™ Taq (TAKARA), 2.5 mM $MgCl_2$, 0.3 mM dNTPs, and enzyme-supplemented buffer: denaturing at 98° C. for 60 seconds, followed by 30 cycles of 98° C. for 20 seconds, and 68° C. for 120 seconds. The PCR reaction product was electrophoresed on an agarose gel, the portion containing the amplified fragment was excised, and then purified. The nucleotide sequence of the resulting DNA fragment was determined and translated to amino acids, then the isolated gene (clone 106) was found to be 33% homologous at the amino acid level with the *Drosophila* twisted gastrulation gene (TSG) (Mason et al., Genes and Develop. 8:1489–1501) (FIG. 1). *Drosophila* TSG gene is thought to be one of the embryonic dorsal determining factors, and the mutation of this gene prevents differentiation of only dorsal midline cells derived from the mesoderm. This is considerably different to the decapentaplegic (DP) gene, which is also a dorsal determining factor considered to interact with TSG gene, where the differentiation of the entire dorsal region is affected.

EXAMPLE 2

Acquisition of Full-Length cDNA

A cDNA library of a 11.5 day-mouse embryo was synthesized in the same manner as in Example 1 using an oligo dT primer and screened using the cDNA fragment as the probe to obtain the full-length cDNA. 2 µg of the cDNA library was added to 50 µl of DH5α (GIBCO BRL) and left standing for 30 minutes on ice. After applying heat shock for 30 seconds at 42° C., the mixture was allowed to stand for about 2 minutes on ice. After the addition of 300 µl of SOC, the mixture was cultured for 30 minutes at 37° C. The mixture was then seeded into a 10-cm dish LB plate (containing ampicillin) on which a NITROBIND™ Nitrocellulose Transfer membrane (MICRON SEPARATIONS) was placed so as to obtain 30,000–40,000 *E. coli* colonies per plate. The *E. coli* colonies that proliferated on the membrane were transferred to a BIODYNE® A transfer membrane (Pall), and cultivated on the LB plate for several hours. The BIODYNE® A transfer membrane was then used for screening the cDNA library. After denaturing with a denaturing solution (0.5 N NaOH and 0.5 M NaCl) for five minutes, the membrane was neutralized with a neutralizing solution (0.5 M Tris-HCl, pH 7.4 and 1.5 M NaCl). After gently washing with 2×SSC and drying up, the DNA and membrane were cross-linked by irradiating with UV light at 1200 J.

Hybridization was performed according to the following procedure. First, the membrane was pre-hybridized for 2 hours at 42° C. in a hybridization buffer (50% formamide, 4.5% Dextran Sulfate, 0.1 mg/ml of salmon sperm DNA, 6×SSC, and 1% SDS). After labeling with RI using PRIME-IT® (Stratagene) and after heat denaturing, 25 ng of clone 106 DNA to be used for the probe was added to the hybridization buffer and left to stand overnight.

The membrane was washed in two stages. First, the membrane was washed for 10 minutes at 42° C. with a washing buffer (2×SSC and 0.1% SDS), and then for 30 minutes at 55° C. with a washing buffer (0.1×SSC and 0.1%SDS). The membrane washed in this manner was then brought into close contact with an X-ray film and developed by exposing to light at −80° C.

One type of clone was obtained through the above procedure. The clone, which was a 3986 bp cDNA, was found to have an open reading frame (87–752) that encodes 222 amino acids, in which amino acids 1 through 24 were presumed to be the signal sequence. The nucleotide sequence of the cDNA is shown in SEQ ID NO:1, while the encoded amino acid sequence is shown in SEQ ID NO:2.

EXAMPLE 3
Expression Analysis of the cDNA Clone by Northern Hybridization

When Northern hybridization was performed using mouse Multiple Tissue Northern Blot (Clontech) and the cDNA obtained in Example 2 as the probe, signals of about 4.0 kb were found in the heart, lung, liver, and kidney. These signals were also confirmed to be expressed in 9, 10, 11, 12, and 13-day embryos.

INDUSTRIAL APPLICABILITY

The protein and gene discovered in the present invention could be counterparts of *Drosophila* TSG gene in mice, which suggests that they may be functionally similar. Through the investigation of their roles in embryo development, the protein and gene of the present invention may contribute to the elucidation of mechanisms of differentiation and bone formation associated with hematopoietic stem cell generation. In addition, they are also useful as tools for developing therapeutic agents for the treatment of diseases related to immune and hematopoiesis-systems and bone formation.

What is claimed is:

1. An isolated nucleic acid encoding a protein comprising the amino acid sequence of SEQ ID NO:2.

2. An isolated nucleic acid encoding the amino acid sequence of SEQ ID NO:2 or a fragment thereof, wherein the fragment is at least 40% of the length of the sequence shown as SEQ ID NO:2, and the fragment binds to BMP2/4.

3. An isolated nucleic acid encoding a protein that (a) comprises the amino acid sequence of SEQ ID NO:2 in which 5 or fewer amino acids are substituted, deleted, and/or inserted, and (b) binds to BMP2/4.

4. The nucleic acid of claim 1, wherein the nucleic acid encodes a fission protein comprising a first amino acid sequence as shown in SEQ ID NO:2 fused to a second amino acid sequence.

5. A vector into which the nucleic acid of claim 1 is inserted.

6. A vector into which the nucleic acid of claim 2 is inserted.

7. A cultured transformant harboring the nucleic acid of claim 1.

8. A cultured transformant harboring the nucleic acid of claim 2.

9. A cultured transformant harboring the vector of claim 5.

10. A cultured transfonnant harboring the vector of claim 6.

11. A method for producing a polypeptide, the method comprising the stops of culturing the transformant of claim 9 and recovering the protein from the transformant or from the culture supernatant thereof.

12. A method for producing a polypeptide, the method comprising the steps of (a) culturing the transformant of claim 10 and (b) recovering the protein from the transformant or from the culture supernatant thereof.

13. A nucleic acid encoding a fusion protein comprising a first amino acid sequence that has the sequence of residues 25–222 of SEQ ID NO:2 fused to a second amino acid sequence.

14. The nucleic acid of claim 13, wherein the second amino acid sequence comprises any one of the following: glutathione S-transferase, FLAG, six histidine residues, influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, immunoglobulin constant region, β-galactosidase, Green Fluorescent Protein (GFP) and maltose binding protein.

15. The nucleic acid of claim 13, wherein the fusion protein comprises an initiator methionine.

16. The nucleic acid of claim 13, wherein the fusion protein comprises a signal sequence.

17. The nucleic acid of claim 13, wherein the fusion protein further comprises residues 1–24 of SEQ ID NO:2.

18. A vector into which the nucleic acid of claim 13 is inserted.

19. A vector into which the nucleic acid of claim 14 is inserted.

20. A cultured transformant harboring the nucleic acid of claim 13.

21. A cultured transformant harboring the vector of claim 18.

22. A cultured transformant harboring the vector of claim 19.

23. A method for producing a protein, the method comprising the steps of culturing the transformant of claim 20 and recovering the fusion protein from the transformant or the culture supernatant thereof.

24. An isolated nucleic acid comprising the coding region of the nucleotide sequence of SEQ ID NO:1.

25. An isolated nucleic acid encoding a protein that (a) has at least 95% identity to the amino acid sequence of SEQ ID NO:2, and (b) binds to BMP2/4.

26. The nucleic acid of claim 25, wherein the protein has at least 98% identity to the amino acid sequence of SEQ ID NO:2.

27. The nucleic acid of claim 25, wherein the protein has at least 99% identity to the amino acid sequence of SEQ ID NO:2.

28. An isolated nucleic acid that encodes a protein comprising residues 25–222 of SEQ ID NO:2.

29. The nucleic acid of claim 28, wherein the protein consists of residues 25–222 of SEQ ID NO:2 with an initiator methionine or a signal peptide.

30. The nucleic acid of claim 28, wherein the protein consists of the amino acid sequence of SEQ ID NO:2.

* * * * *

UNITED STATES PATENT AND TRADEMARK OFFICE
CERTIFICATE OF CORRECTION

PATENT NO. : 6,890,735 B2
DATED : May 10, 2005
INVENTOR(S) : Toshio Kitamura and Sumiyo Morita It is certified that error appears in the above-identified patent and that said Letters Patent is hereby corrected as shown below:

<u>Title page,</u>
Item [56], References Cited, U.S. PATENT DOCUMENTS,
delete "Brennan", insert -- Brennan et al. --
OTHER PUBLICATIONS,
"Nosaka et al.", reference, delete "Moecular", insert -- Molecular --.

<u>Column 31,</u>
Line 34, delete "fission", insert -- fusion --.
Line 47, delete "transfonnant", insert -- transformant --.
Line 50, delete "stops", insert -- steps --.

Signed and Sealed this

Twenty-first Day of March, 2006

JON W. DUDAS
*Director of the United States Patent and Trademark Office*

SEQUENCE LISTING

<160> NUMBER OF SEQ ID NOS: 5

<210> SEQ ID NO 1
<211> LENGTH: 3986
<212> TYPE: DNA
<213> ORGANISM: Mus musculus
<220> FEATURE:
<221> NAME/KEY: CDS
<222> LOCATION: (87)...(752)

<400> SEQUENCE: 1

```
cgcgggagct gcttggaggc tcggcggccg ggaggaggcc ggggccacgc ttcttggaag      60
ctactgagtg acttctttga agaacc atg aag tca cac tat att gtg cta gct     113
                             Met Lys Ser His Tyr Ile Val Leu Ala
                              1               5 cta gcc tcc ctg acg ttc ctg ctg tgt ctc ccc gtg tcc cag agc tgt     161
Leu Ala Ser Leu Thr Phe Leu Leu Cys Leu Pro Val Ser Gln Ser Cys
 10              15                  20                  25 aac aaa gca ctc tgt gcc agc gat gtg agc aaa tgc ctc att cag gag     209
Asn Lys Ala Leu Cys Ala Ser Asp Val Ser Lys Cys Leu Ile Gln Glu
                 30                  35                  40 ctc tgc cag tgc cgg cct gga gaa ggg aac tgc ccc tgc tgt aag gag     257
Leu Cys Gln Cys Arg Pro Gly Glu Gly Asn Cys Pro Cys Cys Lys Glu
             45                  50                  55 tgc atg ctg tgc ctc ggg gcc ctg tgg gac gag tgc tgc gac tgt gtc     305
Cys Met Leu Cys Leu Gly Ala Leu Trp Asp Glu Cys Cys Asp Cys Val
         60                  65                  70 ggt atg tgc aac cct cgg aat tac agc gac acc ccg ccc aca tcc aag     353
Gly Met Cys Asn Pro Arg Asn Tyr Ser Asp Thr Pro Pro Thr Ser Lys
     75                  80                  85 agc acc gtg gag gag ctg cac gag ccc att ccg tcc ctg ttc agg gcg     401
Ser Thr Val Glu Glu Leu His Glu Pro Ile Pro Ser Leu Phe Arg Ala
 90                  95                 100                 105 ctg acg gag ggc gac acc cag ctg aac tgg aac atc gtc tcc ttc cct     449
Leu Thr Glu Gly Asp Thr Gln Leu Asn Trp Asn Ile Val Ser Phe Pro
                110                 115                 120 gtg gca gag gag ctg tca cac cat gaa aac cta gtc tcc ttc cta gaa     497
Val Ala Glu Glu Leu Ser His His Glu Asn Leu Val Ser Phe Leu Glu
            125                 130                 135
```

```
act gtg aac cag ctg cac cac caa aac gtg tct gtt ccc agc aac aat      545
Thr Val Asn Gln Leu His His Gln Asn Val Ser Val Pro Ser Asn Asn
        140                 145                 150 gtc cac gcc ccc ttc ccc agc gac aaa gag cgc atg tgc aca gtg gtt      593
Val His Ala Pro Phe Pro Ser Asp Lys Glu Arg Met Cys Thr Val Val
    155                 160                 165 tac ttt gat gac tgc atg tcc atc cac cag tgt aag ata tcc tgc gaa      641
Tyr Phe Asp Asp Cys Met Ser Ile His Gln Cys Lys Ile Ser Cys Glu
170                 175                 180                 185 tcc atg ggt gca tcc aag tat cgc tgg ttt cac aac gcc tgc tgc gag      689
Ser Met Gly Ala Ser Lys Tyr Arg Trp Phe His Asn Ala Cys Cys Glu
                190                 195                 200 tgc atc ggt cca gag tgc att gac tat ggg agt aaa act gtc aag tgt      737
Cys Ile Gly Pro Glu Cys Ile Asp Tyr Gly Ser Lys Thr Val Lys Cys
            205                 210                 215 atg aac tgc atg ttt taaagagggg aagaaatgc aaaccaaagc agtaagtcat       792
Met Asn Cys Met Phe
        220 gaagtgtgca gaaatcttgg ttctggtatg ctaggagtgt gttaagttat atgattgtaa    852 ctgtgctttt tatatctggt gcctattagt gtaggtcttt tccattggat tcaatggaac    912 tttagtcaca tgaggatcgg gagttcagag gagtcctggg aaaacctgac atgctgacag    972 aaggtgccgt cttcttccag cttttccaaac acttctcgtt ttgaacgtga tagcacaagc   1032 ctggtacatg tgtggttctc acctgccagt tgtagaacac taggtcccta tagtcacaca    1092 tctcttaatt gtgccttggc tggcttacct gttttgtatg agtaaatatt acagtttata    1152 attctaacaa ctcacattca agccatgctg aaacttaatt tcaaaccact ttacattggt    1212 tttagaaagt aaaatatttac tatattttac aacagaagag ttttgcctag ggccagcgag   1272 ctgactcagt ggataaaggc gcttgctacc aagcctgata acctgagttc catccccaga    1332 gcccgtacag tggaaggaca ggaccagctg ctgggagttg tcctctgacc tccagacagg    1392 cacagtatca tgcgtggagg tgtgcttgtg tgtgcacaca cataactaac tgtttttaaa    1452 aatataaacc tcttacatgg tgaaatctaa atctgtcgtg tagctctcac actgacagtg    1512 gtttggatgt tatgtcccct gtccgcctgt agtgctggtg tggtgagaca cagagtcgtc    1572 actgctctgg tatagaagag ttttgtctac caagagtgtc atggcatacc tttgaactt     1632 catcaaatgc acttgaggat gacctgggtc aggaagtagc caggtaaaag cagcgggact    1692 gtaggcgatg ctccattaga ctccgtgcag agcagcaggt gcacagcata gctgggtgtg    1752 cggctgacca ggagagggtc tgactccgca ccagcagaac agcagggtct ccagcacgtg    1812 tgggaagcac gtgggagagg gttgaggaag gatgcacaga tgtggacaga gaagcataaa    1872 aatgtcggga actcctagta gggtccacct taaaatcgct ttatagtctc tggctttgtt    1932 actctgtaag attacacttg ttttctggata tctgaatcca aataagcatc atattttaag   1992 aagctctgtt tctgaacttc caggggggaaa tctgtttaat gtgtttactc ctagcatact   2052 acagaatttt ctagctctat agcttcttac ctagcgtttc catagtgctg agcttcatta    2112 ctacacgccc ttcctagtaa taaaattctc accttcaagc atgaatcaaa acaaatatc    2172 tataatacac aggttcaatt ttatagaatt gctattttct ctagtgcata tctcattaaa    2232 agtaactttt taggaataat ctttatatgg gtacatattt tggtacataa aatagaaaat    2292 gttcttaaac tcattttgta ttatttgaat agttacaaga tgatttgtgg tatcatgggt    2352 acccattata aaccatgctc ttcccagtag ctgacgaact caaggtatca cagccttcta    2412 agaagccgac ttagaacatg gctgtacatg aatattatac attaaggtgt cctctcactt    2472
```

-continued

```
ctacccagag tgcctctgtt caaaggtgcc ttggaaacat ttcagcccct tccttcttag      2532
ctcccacagg gctgtgggtg ttcttgaaat caggaggcgt tttgaaggac cacagctgct      2592
ccatttcagc cgctgattct taggaaagtt catgctctga cagaagtgtg ctttgatggc      2652
ttctagcggt gcatctcgtc tcgttttctt tgtttgtttt tgttgttgct atcatggttt      2712
ggtttggttt tgagacagga tctctgtgca gccctggctg gcctggaatg tactatgtag      2772
accaggctgg ctctcctcat gttttcttag tgatggccat aaacattgtt aaaatacatc      2832
accatctttt aaaaactttt cattattaaa atttaaaata tagcatgtca tttttttacc      2892
ccatacattt gctatgaaaa attttttaaa ccacctgctt taactttttt attgccctgt      2952
ttttcctatt agaattgatc cccactgagg taaattttat aatcatgttt tgtgtatttt      3012
tcctggctcg ccaaggctta tgaagaaata gcagccattc cctgacaggt ttgcgctccc      3072
accacagaga ggctgagcaa gatgatcaga ggatcaaggc cagccagagc aaggcactgc      3132
ccagaaagca caagtcctgt gctcagcgtt ttgcgtagcg ttttattcct aattgaaatg      3192
taatatttca gaagctagca gcctcgctca gtctagacct tccacaccaa tctagcagcg      3252
attctcccgt actaaagcct ttgtaagagt ttacggttct tcctcagtga aaatgatct       3312 tgttttcctt acagccggat ccaaagacgc tagatgttaa gggctgaggc tgaagcccgg      3372
tgacggggcg ctcacctgtc atggtgcagc cctcgttcca ccgtgagcac cagcaagaga      3432
caaacacaag cttgtgagtc agaggccgtt attaaattca tacgcacata ctccctatag      3492
cgagacatgg gcttatgggc aggcttttt tttcataaca tttatgagaa acaatgtttt       3552
tccccataac atttaattag gactgtagct tattggtaat taaggtacaa aatcaaagtc     3612
gagtagaatg tactgttcac acagcgtgtt gtgaaagggg tcctcacacc aaagtttaac      3672
tgtaaagttt agaaaaataa cattgtcatt agcatatttg aacacatatt tggaatttct      3732
aaaaagcatc aaaatagaaa aagaaagtga aactctggag aatgagatgc tgaagatggg      3792
ctatgattta aaggtctgtt ctgtagttag aaagcacctt ttaaagactt tgttcattcc      3852
caagagtcta tgttgattgc atttaacatg accgacaact tatatatgta attgtgtaca      3912
ttttcattgg ttgtctctgt agtccaaaag aaggtatttt aataaaaaat agaaatgact      3972
gtgaaaaaaa aaaa                                                        3986
```

<210> SEQ ID NO 2
<211> LENGTH: 222
<212> TYPE: PRT
<213> ORGANISM: Mus musculus

<400> SEQUENCE: 2

```
Met Lys Ser His Tyr Ile Val Leu Ala Leu Ala Ser Leu Thr Phe Leu
 1               5                  10                  15

Leu Cys Leu Pro Val Ser Gln Ser Cys Asn Lys Ala Leu Cys Ala Ser
            20                  25                  30

Asp Val Ser Lys Cys Leu Ile Gln Glu Leu Cys Gln Cys Arg Pro Gly
        35                  40                  45

Glu Gly Asn Cys Pro Cys Cys Lys Glu Cys Met Leu Cys Leu Gly Ala
    50                  55                  60

Leu Trp Asp Glu Cys Cys Asp Cys Val Gly Met Cys Asn Pro Arg Asn
65                  70                  75                  80

Tyr Ser Asp Thr Pro Pro Thr Ser Lys Ser Thr Val Glu Glu Leu His
                85                  90                  95
```

```
Glu Pro Ile Pro Ser Leu Phe Arg Ala Leu Thr Glu Gly Asp Thr Gln
            100                 105                 110

Leu Asn Trp Asn Ile Val Ser Phe Pro Val Ala Glu Glu Leu Ser His
        115                 120                 125

His Glu Asn Leu Val Ser Phe Leu Glu Thr Val Asn Gln Leu His His
    130                 135                 140

Gln Asn Val Ser Val Pro Ser Asn Asn Val His Ala Pro Phe Pro Ser
145                 150                 155                 160

Asp Lys Glu Arg Met Cys Thr Val Val Tyr Phe Asp Asp Cys Met Ser
                165                 170                 175

Ile His Gln Cys Lys Ile Ser Cys Glu Ser Met Gly Ala Ser Lys Tyr
            180                 185                 190

Arg Trp Phe His Asn Ala Cys Cys Glu Cys Ile Gly Pro Glu Cys Ile
        195                 200                 205

Asp Tyr Gly Ser Lys Thr Val Lys Cys Met Asn Cys Met Phe
    210                 215                 220

<210> SEQ ID NO 3
<211> LENGTH: 19
<212> TYPE: DNA
<213> ORGANISM: Artificial Sequence
<220> FEATURE:
<223> OTHER INFORMATION: Artificially  Synthesized Primer Sequence

<400> SEQUENCE: 3
gggggtggac catcctcta                                                    19

<210> SEQ ID NO 4
<211> LENGTH: 20
<212> TYPE: DNA
<213> ORGANISM: Artificial Sequence
<220> FEATURE:
<223> OTHER INFORMATION: Artificially  Synthesized Primer Sequence

<400> SEQUENCE: 4
cgcgcagctg taaacggtag                                                   20

<210> SEQ ID NO 5
<211> LENGTH: 225
<212> TYPE: PRT
<213> ORGANISM: Drosophila melanogaster

<400> SEQUENCE: 5

Met Gln Leu Leu Cys Tyr Phe Val Ile Leu Phe Val Gly Ile Ala Pro
  1               5                  10                  15

Trp Ser Ser Leu Ala Asn Asp Asp Gly Cys Asn Glu Val Val Cys Gly
            20                  25                  30

Ser Val Val Ser Lys Cys Leu Ile Thr Gln Ser Cys Gln Cys Lys Leu
        35                  40                  45

Asn Asp Cys His Cys Cys Lys Asp Cys Leu Asn Cys Leu Gly Glu Leu
    50                  55                  60

Tyr Ile Glu Cys Cys Gly Cys Leu Asp Met Cys Pro Lys His Lys Asp
 65                 70                  75                  80

Val Leu Pro Ser Leu Thr Pro Arg Ser Glu Ile Gly Asp Ile Glu Gly
                85                  90                  95

Val Pro Glu Leu Phe Asp Thr Leu Thr Ala Glu Asp Asp Glu Gly Trp
            100                 105                 110

Ser Thr Ile Arg Phe Ser Met Arg Ala Gly Phe Lys Gln Arg Val Gln
        115                 120                 125
```

-continued

```
Gly Gly Ala Ser Gly Asp Ala Gly Asn Gly Asn Gly Asn Gly Asn Ala
    130             135             140

Gly Ser Ala Gly Val Thr Leu Cys Thr Val Ile Tyr Val Asn Ser Cys
145             150             155             160

Ile Arg Ala Asn Lys Cys Arg Gln Gln Cys Glu Ser Met Gly Ala Ser
            165             170             175

Ser Tyr Arg Trp Phe His Asp Gly Cys Cys Glu Cys Val Gly Glu Asn
            180             185             190

Cys Leu Asn Tyr Gly Ile Asn Glu Ser Arg Cys Arg Gly Cys Pro Glu
        195             200             205

Asp Gln Asp Gln Leu Leu Thr Ala Asp Thr Val Pro Ala Glu Ala Glu
    210             215             220

Gln
225
```